United States Patent [19]
Aaltonen et al.

[11] Patent Number: 6,143,330
[45] Date of Patent: Nov. 7, 2000

[54] COMPOSITIONS FOR INHIBITING DENTAL CARIES AND/OR MIDDLE EAR INFECTIONS AND USES THEREOF

[76] Inventors: Antti Sakari Aaltonen, Marttilantie 2as.6, FIN-03850 Pusula, Finland; Jouko Suhonen, 663 Garth Ct., Yorktown Heights, N.Y. 10598

[21] Appl. No.: 09/068,393

[22] PCT Filed: Nov. 11, 1996

[86] PCT No.: PCT/FI96/00610

§ 371 Date: Aug. 24, 1998

§ 102(e) Date: Aug. 24, 1998

[87] PCT Pub. No.: WO97/17089

PCT Pub. Date: May 15, 1997

[30] Foreign Application Priority Data

Nov. 9, 1995 [FI] Finland ..................................... 955389

[51] Int. Cl.[7] .......................... A61K 35/20; A61K 35/16; A61K 45/00; A61K 39/395; A61J 7/00

[52] U.S. Cl. .................... 424/535; 424/184.1; 424/187.1; 424/282.1; 424/278.1; 424/130.1; 424/435; 424/529; 424/530; 424/531; 424/93.3; 604/77; 604/76

[58] Field of Search ................................ 424/282.1, 535, 424/93.3, 184.1, 278.1, 187.1, 529, 530, 531, 435, 130.1; 604/77, 76

[56] References Cited

U.S. PATENT DOCUMENTS

| 4,284,623 | 8/1981 | Beck . |
| 4,324,782 | 4/1982 | Beck . |
| 4,636,384 | 1/1987 | Stolle et al. . |
| 4,748,018 | 5/1988 | Stolle et al. . |
| 4,919,929 | 4/1990 | Beck . |
| 5,017,372 | 5/1991 | Hastings . |
| 5,380,198 | 1/1995 | Suhonen . |
| 5,395,392 | 3/1995 | Suhonen . |
| 5,719,196 | 2/1998 | Uhari et al. . |
| 5,772,999 | 6/1998 | Greenblatt et al. . |
| 5,993,413 | 11/1999 | Aaltonen et al. . |

FOREIGN PATENT DOCUMENTS

| 0 064 103 | 11/1982 | European Pat. Off. . |
| 0 127 712 | 12/1984 | European Pat. Off. . |
| 0 336 694 | 10/1989 | European Pat. Off. . |
| 0 479 597 | 4/1992 | European Pat. Off. . |
| 4211613 | 3/1992 | Japan . |
| 91/04727 | 4/1991 | WIPO . |
| 94/00149 | 1/1994 | WIPO . |

OTHER PUBLICATIONS

R. Fulghum et al., "Mongolian Gerbil Tympanic Membrane; Normal and With Induced Otitis Media," *Archives of Otolaryngology*, May 1987, 113; 521–525.

J. Suhonen et al., "Release of Preventive Agents from Pacifiers in Vitro. An Introduction to a Novel Preventive Measure," *Schweiz. Monatsschr. Zahnmed.*, 1994, 104; 945–51.

*Primary Examiner*—Nita Minnifield
*Attorney, Agent, or Firm*—Evenson, McKeown, Edwards & Lenahan, P.L.L.C.

[57] ABSTRACT

Compositions for treating or preventing dental caries and/or middle ear infections. These compositions comprise antibodies to dental caries and/or antibodies to bacteria causing middles ear infections and/or an agent preventing the adhesion, accumulation or reproduction of the pathogens of tooth or middle ear. The preferred agent is xylitol. Methods for using these compositions are also included.

23 Claims, 2 Drawing Sheets

COMPOSITIONS FOR INHIBITING DENTAL CARIES AND/OR MIDDLE EAR INFECTIONS AND USES THEREOF

This application is a 371 of PCT/FI96/00610, filed Nov. 11, 1996.

This invention relates to an immune milk preparation for the prevention of middle ear infections (otitis media) in children. The preparation contains antibodies produced against bacteria which cause middle ear infections and, if desired, also dental caries inhibiting agents.

So called immune milk can be produced by vaccinating a pregnant cow against certain pathogens whereby the cow organism forms antibodies to these diseases, which antibodies are transferred to the colostrum. The remedying effects of immune milk have been known for a long time. Already since the beginning of the century immunized goat or cow milk has been tested in the treatment of various bacterial and viral diseases. The most important of the more recent studies are concentrated on the diseases dependent on the microbes of the gastrointestinal tract, i.a. rheumatoid arthritis, dental caries, gingivitis, diarrheas, dysentery, gastritis and cryptosporidiosis. A dental caries inhibiting product of immunized cow's milk, which contains specific antibodies to killed *Streptococcus mutans* cells, is known (U.S. Pat. No. 4,324,782). In the United States usual immune milk is produced by maintaining the antibody level with boosters. The amount of antibodies is rather small, and the effect is based on daily administration. In Taiwan immune milk is sold as a health drink. In Australia powder containing antibodies to rotavirus has been mixed into i.a. infant formulas (Murtomaa-Niskala, 1994). Whole milk products also contain non-specific antibacterial factors which may have effect of microbial flora (Takahashi et al., 1992).

In Finland immune milk has been prepared against i.a. *Helicobacter pylori* infection (Oona et al., 1994), and antibodies to *Streptococcus mutans* and *Streptococcus sobrinus*, obtained from the colostrum of an immunized bovine (Loimaranta et al., 1996), have been studied at the Dental Department of the University of Turku (Prof. Jorma Tenovuo, personal communication). This immune milk has been produced at the Centre of Agricultural Research in Jokioinen.

An anti-mutans streptococci antibody preparation, isolated from immune colostrum, has been shown to inhibit infection of tooth surfaces by mutans streptococci and to protect teeth from caries when added to a cariogenic diet of gnotobiotic rats (Michalek et al., 1987). The use of a lyophilized, on the same technique based immune whey powder dissolved in water for rinsing of mouth for a minute mornings and evenings for a fortnight significantly reduced the proportion of *S. mutans* in dental plaque of young adult humans as compared to the control group (Filler et al., 1991). However, rinsing out is not a suitable way of administration for small children who, however, would probably most benefit from an increased immune protection (Aaltonen et al., 1987).

Suhonen (1992) has presented the theoretical background for the use of a pacifier like administration device which slowly releases fluorides, xylitol, monoclonal caries antibodies or components of lactoperoxidase system into the mouth, in a prophylactic method for the prevention of dental caries. The operability of a dispensing pacifier as a releaser of sodium fluoride, xylitol and sorbitol from a tablet has been established in vitro, and the administration of passive vaccines via a pacifier against microbes which cause oral diseases has been suggested (Suhonen et al., 1994). A pacifier prototype for dispensing sodium fluoride, xylitol and sorbitol has in our field trial in the Lohja District Health Centre with children of 16 months of age proved to be a functioning means with potential for development for the treatment of diseases of the mouth and throat of children in the sucking-age. In our follow-up study it became evident that the group where children well accepted the test pacifier showed significantly less frequently middle ear infections before 18 months' age (48% versus 78%) than the comparable group which for some reason or another did not use the test pacifier (Suhonen J., Aaltonen A. S., Tenovuo J., "Fall-asleep pacifier in toddlers subject to cariologic risk factors", Poster, The 15th Congress of International Association of Pediatric Dentistry, Gothenburg 1995).

Theoretically it is possible that the children who accepted the test pacifier had so few middle ear infections due to the fact that xylitol which was slowly released from the pacifier and was left to affect in the mouth for a long time when the child fell asleep, would have prevented the growth of *Streptococcus pneumoniae* bacterium (a pneumococcus) in children's throat (Sipponen, 1995, Kontiokari et al., 1995). Over one half of the middle ear infections (otitis media) of bacterial origin in children under 2 years of age are due to pneumococci. A second, fairly common pathogen in middle ear infections is the non-typeable (non-type b) bacterial species *Haemophilus influenzae*, and a third, more infrequent is *Branhamella* (*Moraxella*) *catarrhalis*. In a two-month study with day-care children, the chewing of xylitol chewing gum for 5 minutes 5 times a day has decreased middle ear infections by 50% compared to a control group which used the corresponding chewing gum sweetened with sugar (Uhari et al., 1996). One possible way of explaining the effect is that xylitol would have decreased the adhesion of pneumococcus and also *H. influenzae* on mucosal cells and thus prevented the climb of these ear pathogens through the auditory tube to the middle ear (Assistant Prof. Matti Uhari, personal communication Aug. 11, 1996; Andersson et al., 1986).

In our study middle ear infection was significantly more frequent in those children who had sucked milk or milk gruel from a night bottle at the age of 12–14 months than in those who had sucked juice or water. This and the previous observation, possibly connected with xylitol, indicate that the effect of agents administered via a pacifier may extend to the nasopharyngeal flora and therefrom up to the middle ear. Some of our results indicate that children would obtain their middle ear infections causing bacteria via salivary contacts through the mouth although the main location of these bacteria is considered to be the nasopharynx. The oral cavity can thus be an area of primary defence in the battle against bacteria aiming at the middle ear. It is thus possible that if the above described Suhonen's method of caries prophylaxis is widened to apply to the pathogenic microbe flora of the pharyngeal area, with an administration device known from the method or a device modified therefrom also agents acting against the pathogens of middle ear infections may be administered for a prolonged term, aiming at preventing middle ear infections in children.

For the treatment of children's acute middle ear infections are nowadays used primarily antibiotics, and ear drum puncture and ear drops are used for the immediate removal of pain. The abundant use of antibiotics is feared to promote the prevalence of resistant bacterial strains (Bacuero and Loza, 1994) and selection of the oral microbe flora so that species producing proteases, which degrade immunoglobulin A (IgA), would become more frequent at the expense of others (Østergaard, 1983). Children repeatedly exposed to infections of respiratory tract have in the saliva significantly less IgA than healthy controls (Lehtonen et al., 1987). Due to the high incidence of the disease and the difficulties connected with the treatment, parenteral, serum specific IgG immune response actively increasing vaccines are being developed against the disease. In the future use may be also made of active viral vaccines given as nasal sprays, which stimulate secretory IgA response on the mucous membrane, thus reducing the hazard of a middle ear infection. The idea that middle ear infections in children could be prevented by a passive, outside the human body produced and especially by means of a sucking device for a prolonged time administrable vaccine, has not been, as fas as is known, published previously. Nasally administered IgG-type antibodies to *Haemophilus influenzae* type b capsular polysaccharides have inhibited the nasopharyngeal colonization of this pathogen in infant rats (Kauppi et al., 1993).

The prophylactically used immune milk product, i.e. the anti-otitis immunoglobulin product of bovine colostrum, which is the object of the invention, would complement a passive immune defence, which would correspond in nature mainly to the immune protection obtained from mother's breast milk, however, with the difference that human milk contains mainly IgA-type antibodies, bovine milk IgG-type antibodies. In EP patent application no. 0 479 597 it is disclosed that immunoglobulin of human or bovine milk may be used in the treatment of e.g. middle ear infection, but the application deals expressly with IgA. Characteristic to most bacteria which cause middle ear infections is that they produce proteases that degrade IgA, thus acquiring themselves an ecological survival advantage in the microflora of the throat. The proteases in question do not degrade IgG-type antibodies. The occurrence peak of acute middle ear infections is right at the most eager age of using a pacifier during the latter half of a child's first year of life. A passive IgG-type vaccine delivered by an oral administration device or otherwise orally could be an effective help in the battle against ear pathogens which infect via the mouth and degrade IgA enzymatically.

The chemical and biological properties of antibodies, which belong to whey proteins of milk, are rather well known. One liter of colostrum contains 40–100 grams of antibodies but the same amount of milk only 0.5–1 grams. With the help of the modern methods of dairy technology antibodies may be concentrated, isolated pure and also dried without altering their activity to any significant extent. Antibodies are fully water soluble, odourless and tasteless proteins. A concentrate or powder, which contains antibodies, may be added to different milk products, special food products or clinical nutritive preparations (Korhonen, 1992). Although bovine milk, and thus also the natural or with immunization produced antibodies therein, is a common nutrient, its use in infants is connected with certain disadvantages, which have been diminished in infant formulas and the more extendible minimization of which is obtainable in an immune milk product, to which only the whey protein antibodies of the components of milk are necessarily needed. Antibodies or in other words immunoglobulins of milk relatively seldom cause allergization of children. Milk allergy is developed to about two percent of Finnish children, usually during the first year of life, and the by far frequent reason thereto are the casein components of milk which have been removed from the whey product.

The termination or the small amount of breast feeding during the first three months and allergic disposition seem to predispose children to recurrent ear infections. When the most allergizing factors have been removed from the immune milk product, it may probably be given to a child since a rather small age immediately after the termination of breast feeding or when an infant formula is used as a supplemental feeding. A prophylactic pacifier inhibiting the growth of pathogenic bacteria of the ear would in fall-asleep situations be better than a milk bottle, which as such can predispose to ear infections. In our study those who used the test pacifier reduced the use of a night bottle more than others (Suhonen et al., 1995).

The health of immune milk producing cows is to be tested and they have to be attended with a very special care. Dried immune milk powder has also nutritional importance as it contains whey proteins and in addition usually some amount of lactose for the stabilization of proteins and for adding taste. By hydrolysis lactose can be further split into galactose and glucose, the sugars which are more easily absorbed from the intestine and increase the sweetness of the product. Lactose promotes the health of baby's intestine by maintaining an acidophilic Bifidobacterium flora (Korpela, 1992). However, milk sugars cause dental caries during a prolonged use.

Children's proneness to dental caries depends on whether the bottoms of small pores on the smooth surfaces or on the occlusal fissures of the erupting teeth are covered with a cariogenic or non-cariogenic microbial flora (Svanberg and Loesche, 1977). A cariogenic plaque is formed if mutans streptococci (MS), which produce acids and long chain polysaccharides from sugar, are established in the flora. The development of caries lesions in MS positive children is a multicausal process but it is primarily regarded as being connected with the prolonged exposure to saccharose in the oral cavity (Gustafsson et al., 1953, Aaltonen 1991, Grindefjord et al., 1995a,b). Also other sugars, such as lactose in prolonged breast feeding when the amount of milk calcium and buffering phosphates has already decreased, increase caries risk (Matee et al., 1992). As the resistance of the host and the virulence of the pathogen may vary depending on or irrespective of the environmental factors (Aaltonen, 1989, 1991, 1992, Aaltonen and Tenovuo, 1994), on the individual level it cannot be known beforehand, whether a small baby is going to be an MS carrier and thus a probable caries patient when deciduous teeth are emerging, or not. Therefore cariogenic sugars are to be removed from the immune milk product according to our invention. Another, and process technically good alternative is to add into the product enough protective agents to inhibit attachment (adhesion) of mutans streptococci, accumulation (aggregation) of plaque, production of acid or other virulence factors. Third alternative is to turn to remineralizing agents, which inhibit the damaging symptom of caries disease, the demineralization of teeth, of which agents the effect of fluorides has been known for over half a century.

In our parallel patent application (PCT/FI96/00609; WO 97/17037) we propose a new model of an administration device to be used for the delivery of the immune milk product according to our invention in a prophylactic method for inhibiting middle ear infections in children. The product according to this invention in its different forms may, however, be added also to different food products for small children, thereby obtaining bioactive products which may be administered to children orally by also other means than via above mentioned administration device. By bioactive products is in this connection meant such products which contain biologically effective active agents which are advantageous to human body.

The choice of an antigen for the production of an antibody

By means of an administration device, which slowly releases effective antibodies into the mouth, a relatively sustained effect of the microflora of the mouth and throat is obtained with small doses. It is thus of importance that the antibodies used do not disturb the development of the normal flora which is important to the health of the mouth. In the area of mouth, for example noncariogenic *Streptococcus sanguis* and cariogenic *S. mutans* compete in the colonization of tooth surfaces, and it is not out of question, however, it is not known, that an antigenic structure of a related *S. pneumoniae* (pneumococcus) would be similar to either one, whereby a cross-reacting antibody aimed at the inhibition of an ear pathogenic pneumococcus would affect also on the above mentioned competition situation relating to dental caries. Cross reactions have to be examined in vitro before the product is taken into use, and although combination products obtained by several antigens are in thought tempting, for a clinical use an antibody product directed to only one pathogen species at a time (there could be different strains) should be chosen in order to facilitate the follow-up study. Only when the effect of this has been studied, the assortment can be broadened.

Due to the chemically known safety and easy production of immune milk, the immunogen repertoire may, if necessary, be expanded and adjusted even quickly for example to bacterial strains which have become resistant to antibiotics. In these medical cases the treatment should be based on diagnosis, and the antibodies to be used should be as specific as possible, preferably monoclonally produced.

When selecting an antigen for a large-scale prophylactic use, attention has to be paid to the advantage which probably is obtainable from the new method of treatment as compared to other methods of treatment. As regards ear pathogenic pneumococci, it is to be expected that an octavalent, on a protein carrier conjugated polysaccharide antigen vaccine, which already is on trial in Finland, will to a large degree abolish the problem of middle ear infections due to pneumococci (Giebink, 1994). There remain *Haemophilus influenzae* (non-type b) and *Branhamella* (*Moraxella*) *catarrhalis*, which are more difficult to treat and against which there is no known vaccine. Of these, the former is better known as to its habits of living. Already for a long time ago it has been shown that it lives also in the mouth region, and is a fairly common cause for recurrent middle ear infections in children under 5 years of age. In the throat of those children who are prone to recurrent middle ear infections, *H. influenzae* is found significantly more frequently even during healthy periods than in those of others (Faden et al., 1991). As the association between pharyngeal carriage of *H. influenzae* and antibodies in breast milk seems also to be best documented of the ear pathogens (Harabuchi et al., 1994), taking it as the first object of immune milk prophylaxis seems reasonable. As the immunogenic structures of *H. influenzae* are not so exactly known, the most reliable result is to be expected by using a killed whole cell vaccine. Due to the considerable variation of the nontypeable, usually uncapsulated form (non b) connected with middle ear infections, it would be worth to use several of the strains available simultaneously in the immunization of cows. Pure cultured strains which are prevailing in Finland at the moment are obtainable from the National Public Health Institute of Oulu, where sample material from a cohort study, which is going on in the region of Tampere to study whether babies are carrying ear pathogens in their throat, are collected (Docent Aino K. Takala, personal communication).

In addition to the immunization against *H. influenzae*, immunization of cows is worth trying also with a corresponding vaccine against *B. catarrhalis*. Naturally also the most pathogenic of the *S. pneumoniae* strains to the ear (i.a. 6, 14, 19, 23) come into question, at least in the sense of a comparative study, although an effective parenteral vaccine is to be expected against them. This and also the other known, on a protein carrier conjugated vaccines of multiple valency would probably be very effective also for the production of immune milk in cows.

The long-chain alkyl compound in the polysaccharide-protein conjugate is an immunoadjuvant. A prophylactically used antibody administered by means of an administration device could be suprisingly effective, as it would affect already at the plankton stage of bacterial cells in an early biofilm on the outermost surface of the mucous membrane, where the effect of parenterally produced serum antibodies does not to any significant extent reach.

Preparation and use of vaccine

The pure bacterial strains selected for the preparation of vaccine (cf. above) are grown to cultures large enough by using known microbiological methods. The culture is killed for example by incubating at a suitable temperature until the culture is sterile. Sterility is confirmed from samples after several hours. Killed bacterial cells are washed, centrifuged and lyophilized for storage.

Also formalin may be used for inactivation. In the process the thinness of cell walls of the bacteria in question is taken into consideration, and known laboratory techniques are used trying to keep fimbria etc. possible antigenic structures as intact as possible. Dry cell powder obtained from the most common *H. influenzae* strains (or *B. catarrhalis* strains) found in the nasopharynx is weighed in the same amounts and combined to obtain a polyvalent antigen. Dry cells are then mixed into a physiological saline solution to form a concentrated stock suspension. Dilutions are made therefrom until a certain optical density, which corresponds to the amount of cells suitable for a vaccine, is obtained. The stock suspension is stored frozen in several batches. The final dilution is made according to a previously determined dilution coefficient, and at the same time its sterility is checked. Some accepted adjuvant (e.g. aluminum hydroxide and phosphate, liposomes) is used to assist in the immunization. Vaccination technique is known in veterinary medicine. Cows are vaccinated several times during the dry period before parturition by injecting intramuscularly a suitable amount of antigen suspension. Immunization is followed from serum samples. The immunization of a cow to the antigen used may be ascertained by determining specific antibodies from serum by for example ELISA-method and by comparing the results to a cow vaccinated with placebo. Antibodies of mainly IgG-type are carried in large amounts from serum into colostrum.

Collection and processing of immune milk

Colostrums from 3 to 5 first milkings during two to three days after parturition are collected. From one cow is at its best obtained 50 liters colostrum. A calf drinks about three liters at a time but it can have other, frozen colostrum. A whey-based concentrate which contains the immunoglobulins is separated from the colostrum with a dairy technology already in use. Immune milk can be pasteurized but then about 30% of the activity of antibodies is lost. Antibodies are preserved and a hygienic level high enough is obtained by purifying immune whey with the help of membrane filters (0.2 $\mu$m) and by confirming with microbiological tests that the cows are healthy. The whey product may be lyophilized into a powder. Alternatively spray drying may be used whereby the activity of antibodies is also preserved, if low temperatures are used. Antibodies to the antigen used in the vaccine which the whey powder contains can be determined in the same way as from the serum. In the immune whey product functioning according to the invention significantly increased levels of IgG antibody to H. influenzae (non-type b) specific structure antigen and/or whole cell antigen, or respectively to B. catarrhalis whole cell antigen if it has been used as the vaccine of the cow, can be shown as compared to the one prepared by a placebo vaccine. Known structure antigens of H. influenzae are i.a. protein "e" (FI pat. application 914241) and protein P6 (Harabuchi et al., 1994). The capsular polysaccharide antigens of S. pneumoniae are known, but also for example pneumolysin which is a protein enzyme specific to pneumococcus can be used as a recognition antigen. Immune whey powder contains lactose which stabilizes proteins and facilitates the compression of the powder into a tablet form. It is possible to remove the lactose and replace the same at least partially with xylitol.

Protection against dental caries

For example following agents or groups of agents which are studied in detail in the following may be used against caries in our product:

1. Xylitol ($C_5H_{12}O_6$). In nature xylitol is found in small amounts in almost all fruit and it is a normal intermediate of human metabolism (Touster, 1960, Mäkinen, 1978). Xylitol is not able to generate bacterial acid production wherefore it is a cariostatic agent (Mühlemann et al., 1970, Scheinin and Mäkinen, 1975). In addition to the mentioned cariostatic effect xylitol possesses quite apparent caries inhibiting properties in a prolonged and frequent administration (Isokangas, 1994). Xylitol has been found i.a. to increase the amount of basic amino acids, arginine and lysine, in the tooth plaque. This makes the thriving of caries causing aciduric and acidogenic mutans streptococci in the mouth more difficult (Mäkinen and Isokangas, 1988, Söderling and Scheinin, 1991). Xylitol inhibits the growth of cariogenic S. mutans, lowers the ability of other oral microorganisms to produce acids as well and prevents the biosynthesis of extracellular polysaccharides and lipoteichoic acids, the formation of which belongs to the properties of cariogenic dental plaque.

By using an administration device which slowly releases an active agent it is possible to create around the erupting teeth in the mouth of a sleeping child for hours an oral fluid environment, which according to our study evidently has caries preventing properties. When used this way, the advantageous properties of xylitol are expected to be maximized with rather small doses without laxative side effects. A disadvantage of xylitol and other polyols is especially with small children their slow absorption from the intestine whereby large doses lead to an osmotic diarrhea.

2. Fluorides. Generally, a $F^-$ ion is not believed to affect on the colonization of mutans streptococci (MS) under usual circumstances (Kilian et al., 1979, van Houte et al., 1978, Zickert and Emilson, 1982). According to one theory, however, the fluorides, at least at higher concentrations, prevent the attachment of bacteria on the tooth surface by reducing the adhering electrostatic forces (Rölla, 1997a). Usually the caries-preventing effect of fluorides on the teeth is associated with the ability of fluoride ion to harden the tooth surface and promote remineralization. In addition, the fluoride ion disturbs the carbohydrate metabolism of mutans streptococci, and thus reduces the acid production in the plaque (Hamilton, 1977, Harper and Loesche, 1986). The use of fluorides as a caries protecting agent in an immune milk product is limited by the danger of their overdose. They are not recommended at all to those under 6 months of age, and the maximum dose for those of 6 to 24 months of age is 1 tablet or in other words 0.25 mg $F^-$ per day, to those of 2–7 years of age 2 tablets. Nowadays, when the use of fluorine tooth pastes is common already among small children which may swallow considerable amounts of it, the administration of extra fluorine in the form of another product may be contraindicative. When administered from an administration device held during night, even a fraction of the fluorine amounts of the present fluorine tablets can be effective as via the device a prolonged local effect is obtained on the surface of erupting teeth, which surface in an immature state is prone to colonization by MS and demineralization.

3. Monoclonal caries antibodies. With known hybridoma and gene manipulation techniques it is in principle possible to produce extremely specific antibodies to any virulence factor of MS after it has been identified. Perhaps the hitherto most promising anti-cariotic antibody preparation is a monoclonal IgG1-type antibody to an adhesive protein antigen SA I/II of the MS cell wall (Ma et al., 1990). By treating the teeth with this antibody the prevention of the return of MS in the tooth plaque of adult humans has been successful (Ma and Lehner, 1990). In the serum samples of small children in southwestern Finland, whose teeth were still free of mutans streptococci, was found considerable amounts of IgG-type antibodies to SA I/II antigen (Aaltonen, 1989, Tenovuo et al., 1990). It is apparent that these natural antibodies are able to restrict MS infection of immunized children by influencing via serum fluid which oozes from the gingivae on the surface of an erupting tooth. However, a natural immunization effective enough is exceptional. If the specific antibodies in question would be brought into the mouth of a child in a product according to our invention via the above mentioned administration device when deciduous teeth erupt at the age of ½ to 2½ years, this passive vaccine could in theory inhibit dental caries even at a later age as deciduous teeth would be covered with a mutans-free non-cariogenic microflora, which probably would be carried to permanent teeth and, having an advantage in competition, inhibit even later spreading of MS. Bioactive specific and nonspecific proteins administered from an administration device may become structural parts of the glycoprotein pellicle which is formed on the surface of erupting teeth and the composition of which is important to the colonization of pathogens (Gibbons, 1984).

4. Anti-caries antibodies of immune milk. Immune milk (colostrum) has been produced on our initiative at the Agricultural Research Centre in Jokioinen against cariogenic MS species S. mutans and S. sobrinus (Loimaranta et al., 1996). The anti-MS effect of the immune whey product has been examined in vitro at the Dental Department of the University of Turku (J. Tenovuo, personal communication). The efficiency of a corresponding anti-S. mutans whey product has been shown previously in animal and adult human tests (Michalek et al., 1987, Filler et al., 1991). If the studies in Turku confirm the results obtained previously abroad, antibodies obtained with the same Finnish method would be excellently suitable as caries inhibiting agents for the anti-pneumococci, anti-Haemophilus and anti-Branhamella products according to our invention or for their combinations. However, it would be appropriate to add xylitol to our combination product due to an additive anti-caries and anti-otitis effect which is to be expected as well as due to its stabilizing effect on proteins. An acyclic xylitol stabilizes protein structures by competing with water molecules for the primary hydration layer of proteins and by thus preventing denaturation.

Administration device

We have developed an administration device of a new type for the optimal administration of the anti-otitis immune milk product according to our invention. This device is described in more detail in our parallel patent application PCT/FI96/00...

PRODUCTION OF BOVINE IMMUNE COLOSTRUM

Figure 1:
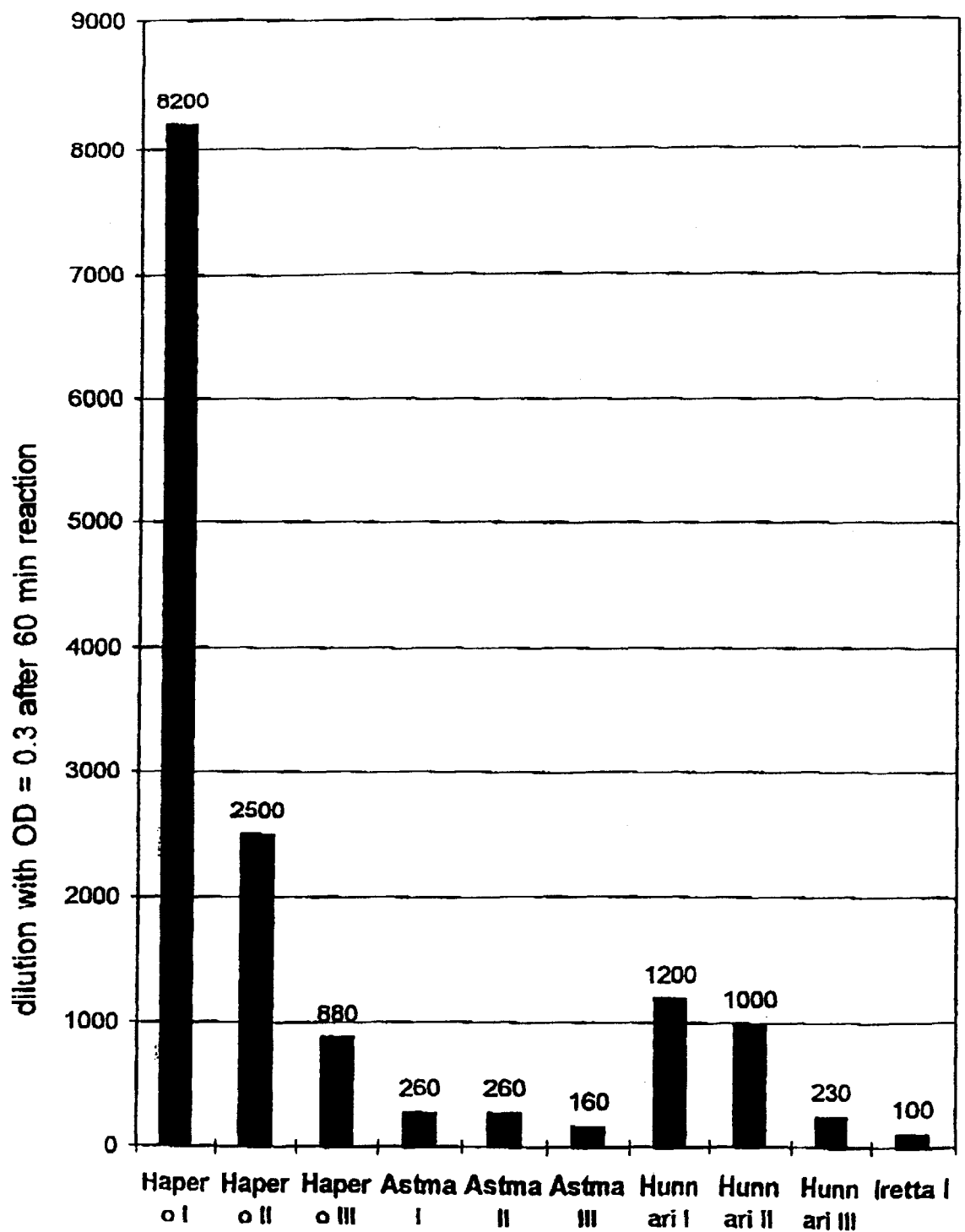
FIG. 1 shows the antibody titers (ELISA) from colostrum of cows immunized against *Haemophilus influenzae* (non-type b) bacteria.
Figure 2:
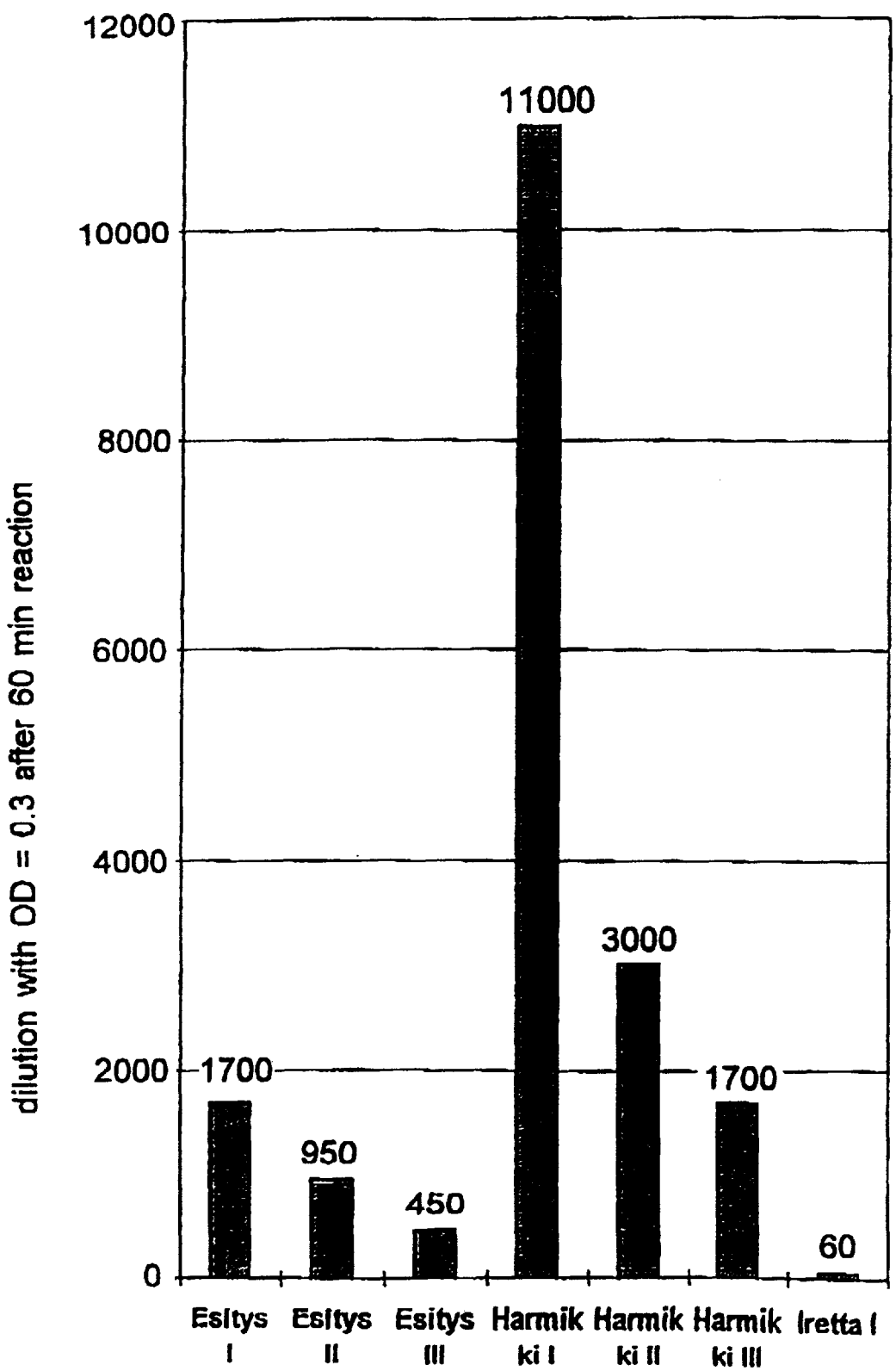
FIG. 2 shows the antibody titers (ELISA) from colostrum of cows immunized against *Streptococcus pneumoniae* bacteria.

At the Agricultural Research Centre in Jokioinen pregnant cows have been immunized with capsular *Streptococcus pneumoniae* and noncapsular (non b) *Haemophilus influenzae* whole cell antigens killed with formalin. The vaccine was prepared at the National Public Health Institute (Helena Käyhty). Cows became reasonably well immunized (antibodies were determined from serum samples), and antibodies were produced in colostrum which is shown by the risen antibody titers found. FIG. 1 shows thus the antibody titers from colostrum of cows (Hapero, Astma, Hunnari) immunized with *Haemophilus influenzae* (nontypeable: IH 57501, IH 57522, IH 57596, IH 57602, IH 57608) to whole cell antigen determined with ELISA test, and FIG. 2 shows, respectively, the antibody titers from colostrum of cows (Esitys, Harmikki) immunized with *Streptococcus pneumoniae* (serotype 4, strains IH 31890, IH 32026) to a serotype specific polysaccharide antigen (ELISA). The cow used as a control (Iretta) received only aluminiumhydroxide adjuvant.

Antibodies can be isolated from the obtained colostrum for example by the method described by Loimaranta et al. (1996). The resulting antibody powder may be used as an active ingredient in the product according to the invention.

It is evident to a person skilled in the art that the embodiments of the invention are not restricted to the examples shown above but may vary within the scope of the appended claims.

REFERENCES

Aaltonen A S. Natural immunity in dental caries. Longitudinal studies of serum and salivary antibodies reactive with *Streptococcus mutans* in young children in relation to dental caries and some material factors. Doctoral thesis, Turku 1989

Aaltonen A S. The frequency of mother-infant salivary close contacts and maternal caries activity affect caries occurrence in 4-year-old children. Proc Finn Dent Soc. 1991, 87, 373–382

Aaltonen A S. Lapsen immunistuminen hammaskariesta vastaan. Suom Hammasl L 1992, 39, 114–118

Aaltonen A S, Tenovuo J. Association between mother-infant salivary contacts and caries resistance in children: a cohort study. Pediatr Dent 1994, 16 11–16

Aaltonen A S, Tenovuo J, Lehtonen O-P. Increased dental caries activity in pre-school children with low baseline levels of serum IgG antibodies against the bacterial species *Streptococcus mutans*. Arch Oral Biol 1987, 32, 55–60

Andersson B, Porras O, Hanson L Å, Lagergård T, Svanborg-Edén C. Inhibition of attachment of *Streptococcus pneumoniae* and *Haemophilus influenzae* by human milk and receptor oligosaccharides. J Infect Dis 1986, 153, 232–237

Bacuero F, Loza E. Antibiotic resistance of microorganisms involved in ear, nose and throat infections. Pediatr Infect Dis J 1994, 13, S9–S14

Faden H, Waz M J, Bemstein J M, Brodsky L, Stanievich J, Ogra P L. Nasopharyngeal flora in the first years of life in normal and otitis-prone children. Ann Otol Rhinol Laryngol 1991, 100 612–615

Filler S J, Gregory R L, Michalek S M, Katz J, McGhee J R. Effect of immune bovine milk on *Streptococcus mutans* in human dental plaque. Arch Oral Biol 1991, 36, 41–47

Gibbons R J. Adherent interactions which may affect microbial ecology in the mouth. J Dent Res 1984, 63, 378–385

Giebink G S. Preventing otitis media. Ann Otol Rhinol Laryngol 1994, 103, 20–23

Grindefjord M, Dahllöf G, Modéer T. Caries development in children from 2.5 to 3.5 years of age: a longitudinal study. Caries Res 1995a (in press)

Grindefjord M, Dahllöf G, Nilsson B, Modéer T. Prediction of dental caries development in 1-year-old children. Caries Res 1995b, 29, 343–348

Gustafsson B R, Quensel C E, Lanke L S, Lundqvist C, Grahnen H, Bonow B E, Krasse B. The Vipeholm dental caries study. Acta Odont Scand 1953, 11, 232–364

Hamilton I R. Effects of fluoride on enzymatic regulation of bacterial carbohydrate metabolism. Caries Res 1977, 11, (suppl 1) 262–291

Harabuchi Y, Faden H, Yamanaka N, Duffy L, Wolff J, Krystofik D. Human milk secretory IgA antibody to nontypeable *Haemophilus influenzae*: possible protective effects against nasopharyngeal colonization, J Pediatr 1994, 124, 193–198

Harper D S, Loesche J. Inhibition of acid production from oral bacteria by fluoroapatite derived fluoride. J Dent Res 1986. 65. 30–33

Isokangas P. Ksylitolin käyttë kouluikäisten kariespreventiossa. Tieteellinen tausta. Fiksu tapa. Valtakunnallinen terveystapahtuma. STAKES, Helsinki 1994, 4–16

Kauppi M, Saarinen L, Käyhty H. Anti-capsular polysaccharide antibodies reduce nasopharyngeal colonization by *Haemophilus influenzae* type B in infant rats. J Infect Dis 1993, 167, 365–371

Kilian M, Thylstrup A, Fejerskov O, Predominant plaque flora of Tanzanian children exposed to high and low water fluoride concentrations. Caries Res 1979, 13, 330–343

Kontiokari T, Uhari M, Koskela M. Effect of xylitol on growth of nasopharyngeal bacteria in vitro. Antimicrob Agents Chemother August 1995, 39(8), 1820–1823

Korhonen H. Immuunimaidosta erityisvalmisteita. Maito ja Me 1992, n:o 10 (Maito 2000), 5

Korpela R. Laktoosi on haaste tuotekehittelylle. Maito ja Me 1992, n:o 10 (Maito 2000), 5

Lehtonen O-P J, Tenovuo, J, Aaltonen A S, Vilja P. Immunoglobulins and innate factors of immunity in saliva of children prone to respiratory infections. Acta Path Microbiol Immunol Scand Sect C 1987, 95, 35–40

Loimaranta V, Tenovuo J, Virtanen S, Marnila P, Suhonen J, Syväoja E-L, Tupasela T, Korhonen H. Generation of bovine immune colostrum against *Streptococcus mutans* and *S. sobrinus* and its effect on glucose uptake and extracellular polysaccharide formation by mutans streptococci. J Dental Res 1996, (in press)

Ma J K-C, Lehner T. Prevention of colonization of *Streptococcus mutans* by topical application of monoclonal antibodies in human subjects. Arch Oral Biol 1990, 35 Suppl 115S–122S Ma J K-C, Hunjan M, Smith R, Kelly C, Lehner T. An investigation into the mechanism of protection by local passive immunization with monoclonal antibodies against *Streptococcus mutans.* Infect Immun 1990, 58, 3407–3414

Matee M I N, Mikx F M H, Maselle S Y M, Palestein Helderman W H van. Mutans streptococci and lactobacilli in breast-fed children with rampant caries. Caries Res. 1992, 26, 183–187

Michalek S M, Gregory R L, Harmon C C, Katz J, Richardsson G J, Hilton T, Filler S J, McGhee J R. Protection of gnoto-biotic rats against dental caries by passive immunization with bovine milk antibodies to *Streptococcus mutans.* Infect Immun 1987, 55 2341–2347

Mühlemann H, Regolati B, Marthaler T. The effect of rat fissure caries of xylitol and sorbitol. Helv Odont Acta 1970, 14, 48–50

Murtomaa-Niskala A. Immuuimaitotutkimus tähtää luonnonmukaiseen hoitoon. Maito ja Me 1994, n:o 6, 17

Mäkinen K K. Biochemical principles of the use of xylitol in medicine and nutrition with special consideration of dental caries. Birkhäuser Verlag, Basel 1978

Mäkinen K K. Isokangas P. Relationship between carbohydrate sweeteners and oral diseases. Prog Food Nutr Sci 1988, 12, 73–109

Oona M, Maaroos H-I, Rago T, Korhonen H, Salminen S. Use of bovine immune colostrum in the treatment of *Helicobacter pylori* infection in children. Poster abstract. Peptic ulcer and gastritis—new infectious diseases IX Medical Symposium of the Yrjö Jahnsson Foundation, Sannäs Finland, Aug. 17–19, 1994

Rölla G. Effects of fluoride on initiation of plaque formation. Caries Res 1977a, 11 (suppl 1), 243–261

Scheinin A, Mäkinen K K. Turku sugar studies I–XXI. Acta Odontol Scand (Suppl 70) 1975, 33, 1–351

Sipponen V. (editor): Ksylitolipurkkaa korvien suojaksi. Hyvä Terveys 1995, n:o 5, 21

Suhonen J. Mutans streptococci and their specific oral target. New implications to prevent dental caries? Schweiz Monatsschr Zahnmed 1992, 102, 286–291

Suhonen J, Sener B, Bucher W, Lutz F. Release of preventive agents from pacifiers in vitro. An introduction to a novel preventive measure. Schweiz Monatsschr Zahnmed 1994, 104, 946–951

Suhonen J, Aaltonen A S, Inkilä-Saari I. Uuden kariesprofylaktisen yötutin hyväksyntä 16 kuukauden ikäisillä riskiryhmään valituilla lapsilla. Hand-out. The dental service of the Lohja District Health Centre Sep. 1, 1995

Svanberg M, Loesche W J. The salivary concentration of *Streptococcus mutans* and *Streptococcus sanguis* and their colonization of artifical tooth fissures in man. Arch Oral Biol 1977, 22, 441

Söderling E, Scheinin A. Perspectives on xylitol-induced oral effects. Proc Finn Dent Soc 1991, 87, 217–230

Takahashi N, Eisenhuth G, Lee I, Schachtele C, Laible N, Binion S. Non-specific antibacterial factors in milk from cows immunized with human oral bacterial pathogens. J Dairy Sci 1992, 75, 1810–1820

Tenovuo J, Lehtonen O-P, Aaltonen A S. Caries development in children in relation to the presence of mutans streptococci in the dental plaque and of serum antibodies against whole cells and protein antigen 1/11 of *Streptococcus mutans.* Caries Res 1990, 24, 59–64

Touster O. Essential pentosuria and the glucuronate-xylulose pathway. Fed Proc 1960, 19, 977–983

Uhari M, Kontiokari T, Koskela M, Niemelä M. Br Med J 1996, 313 1180– van Houte J, Aasenden R, Peebles T C. Oral colonization of *Streptococcus mutans* in human subjects with low caries experience given fluoride supplements from birth. Arch Oral Biol 1978, 23, 361–366

Zickert I, Emilson C G. Effect of a fluoride-containing varnish on *Streptococcus mutans* in plaque and saliva. Scand J Dent Res 1982, 90, 423–428

Øergaard P A. Oral bacterial flora and secretory IgA in small children after repeated courses of antibiotics. Scand J Infect Dis 1983, 15 115–118

What is claimed is:

1. A composition comprising:
   1) IgG-type antibodies specific to one or several bacteria causing otitis; and
   2) one or several dental caries inhibiting agents.

2. The composition of claim 1, wherein the antibodies are obtained from a whey-based part of the colostrum of a healthy cow immunized against a bacterium that causes middle ear infections.

3. The composition of claim 1, wherein the antibodies are to the group consisting of *Haemophilus influenzae* (non-type b), *Streptococcus pneumoniae* and *Branhamella (Moraxella) catarrhalis* bacteria, and combinations thereof.

4. The composition of claim 2, wherein the antibodies are to the group consisting of *Haemophilus influenzae* (non-type b), *Streptococcus pneumoniae* and *Branhamella (Moraxella) catarrhalis* bacteria, and combinations thereof.

5. The composition of claim 1, wherein the dental caries inhibiting agents are from the group consisting of specific antibodies to cariogenic Streptococci and xylitol, and combinations thereof.

6. The composition of claim 5, wherein the specific antibodies are those raised against the group consisting of cariogenic *Streptococcus mutans* and *Streptococcus sobrinus* bacteria, and combinations thereof.

7. The composition of claim 5, wherein the xylitol is used as a cariostatic, a middle ear infection inhibiting sweetener and a protein stabilizing agent.

8. A composition, comprising:
   1) a specific antibody to one or several middle ear infection causing bacteria; and
   2) an agent preventing the adhesion, accumulation or reproduction of the pathogens of tooth or middle ear.

9. The composition of claim 8, wherein the agent preventing the adhesion, accumulation or reproduction of the pathogens of tooth or middle ear is xylitol.

10. The composition of claim 8, wherein the composition is a children's food or a milk-based dairy product.

11. A composition, comprising:
    1) a specific antibody to one or several middle ear infection causing bacteria;
    2) an agent preventing the adhesion, accumulation or reproduction of the pathogens of tooth or middle ear; and
    3) a specific antibody to one or several dental caries causing bacteria.

12. A method of preventing otitis comprising administering an effective amount of an immune milk preparation comprising IgG-type antibodies specific to one or several bacteria causing otitis, and one or several dental caries inhibiting agents.

13. A method of claim 12, wherein the dental caries inhibiting agents are selected from the group consisting of specific antibodies to cariogenic Streptococci and xylitol, and combinations thereof.

14. A method of claim 12, wherein the antibodies are to the group consisting of *Haemophilus influenzae* (non-type b), *Streptococcus pneumoniae* and *Branhamella (Moraxella) catarrhalis* bacteria, and combinations thereof.

15. A method of claim 12, wherein the administration is oral.

16. A composition, comprising:
   1) a specific antibody to one or several dental caries causing bacteria; and
   2) an agent preventing the adhesion, accumulation or reproduction of the pathogens of tooth or middle ear.

17. The composition of claim 16, wherein the agent is xylitol.

18. A method of treating otitis comprising administering an effective amount of xylitol.

19. The method of claim 18, further comprising administering an effective amount of IgG-type antibodies specific to one or several bacteria causing otitis.

20. The method of claim 18, further comprising administering an effective amount of IgG-type antibodies specific to *Streptococcus mutans*.

21. The method of claim 18, wherein the administration is oral.

22. A method of treating or preventing dental carries and otitis comprising oral administering an effective amount of the composition of claim 1.

23. A method of treating or preventing dental carries and otitis comprising oral administering an effective amount of the composition of claim 11.

* * * * *